(12) United States Patent
Colvin, Jr. et al.

(10) Patent No.: US 8,073,548 B2
(45) Date of Patent: Dec. 6, 2011

(54) WRISTBAND OR OTHER TYPE OF BAND HAVING AN ADJUSTABLE ANTENNA FOR USE WITH A SENSOR READER

(75) Inventors: Arthur E. Colvin, Jr., Mr. Airy, MD (US); Benjamin N. McLeod, Reston, VA (US); Casey J. O'Connor, Gaithersburg, MD (US); Burleigh M. Hutchins, Greenfield, MA (US); Colleen Shannon, Mt. Airy, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 431 days.

(21) Appl. No.: 10/923,698

(22) Filed: Aug. 24, 2004

(65) Prior Publication Data

US 2006/0047327 A1   Mar. 2, 2006

(51) Int. Cl.
  *A61N 1/08* (2006.01)
(52) U.S. Cl. ............. 607/60; 607/30; 607/31; 607/32; 607/33; 607/61
(58) Field of Classification Search ............. 600/509, 600/300, 522–523; 607/30–33, 60–61; 128/903
  See application file for complete search history.

(56) References Cited

U.S. PATENT DOCUMENTS

| | | | |
|---|---|---|---|
| 2,255,897 A | 9/1941 | Rebori et al. | |
| 4,003,152 A | 1/1977 | Barker et al. | |
| 4,089,195 A | 5/1978 | Lai | |
| 4,371,945 A | 2/1983 | Karr et al. | |
| 4,419,770 A | 12/1983 | Yagi et al. | |
| 4,656,478 A | 4/1987 | Leuenberger | |
| 4,665,896 A * | 5/1987 | LaForge et al. | ............. 600/17 |
| 4,722,625 A | 2/1988 | O'Brien | |
| 4,754,285 A | 6/1988 | Robitaille | |
| 4,769,656 A | 9/1988 | Dickey | |
| 4,785,294 A | 11/1988 | Campbell | |
| 4,817,196 A | 3/1989 | MacNak et al. | |
| 4,847,818 A | 7/1989 | Olsen | |
| 4,884,252 A | 11/1989 | Teodoridis et al. | |
| 4,922,260 A | 5/1990 | Gaskill et al. | |
| 4,947,432 A | 8/1990 | Topholm | |
| 5,072,231 A | 12/1991 | Koyama | |
| 5,128,686 A | 7/1992 | Tan et al. | |
| 5,132,697 A | 7/1992 | Tan | |
| 5,134,418 A | 7/1992 | Gomez et al. | |
| 5,134,724 A | 7/1992 | Gehring et al. | |
| 5,144,325 A | 9/1992 | Kurcbart | |
| 5,159,713 A | 10/1992 | Gaskill et al. | |
| 5,179,733 A | 1/1993 | Matsui | |

(Continued)

FOREIGN PATENT DOCUMENTS

JP    H04-13314    1/1992

(Continued)

*Primary Examiner* — Niketa Patel
*Assistant Examiner* — Joseph Stoklosa
(74) *Attorney, Agent, or Firm* — Rothwell, Figg, Ernst & Manbec, pc

(57) ABSTRACT

The present invention provides, among other things, a sensor system, having (1) a sensor implanted in a body part of the subject, wherein the sensor has a first antenna, and (2) a sensor reader worn on the subject's body part, wherein the sensor reader has a band housing a second antenna, which is inductively coupled with the first antenna, for enabling the sensor reader to communicate with the sensor.

10 Claims, 14 Drawing Sheets

U.S. PATENT DOCUMENTS

| | | | |
|---|---|---|---|
| 5,189,431 A | 2/1993 | Marinelli | |
| 5,225,846 A | 7/1993 | Koyama | |
| 5,243,356 A | 9/1993 | Hama | |
| 5,265,265 A | 11/1993 | Hama et al. | |
| 5,265,272 A | 11/1993 | Kurcbart | |
| 5,280,296 A | 1/1994 | Tan et al. | |
| 5,280,645 A | 1/1994 | Nguyen et al. | |
| 5,303,421 A | 4/1994 | Goldenberg | |
| 5,317,326 A | 5/1994 | Tay et al. | |
| 5,450,091 A | 9/1995 | Hama | |
| 5,499,398 A | 3/1996 | Kudoh et al. | |
| 5,526,006 A | 6/1996 | Akahane et al. | |
| 5,530,453 A | 6/1996 | Koyama | |
| 5,564,096 A | 10/1996 | Hama et al. | |
| 5,628,324 A * | 5/1997 | Sarbach | 600/483 |
| 5,742,256 A | 4/1998 | Wakabayashi | |
| 5,886,669 A | 3/1999 | Kita | |
| 5,904,708 A * | 5/1999 | Goedeke | 607/18 |
| 5,907,522 A | 5/1999 | Teodoridis et al. | |
| 6,005,525 A | 12/1999 | Kivelä | |
| 6,175,729 B1 | 1/2001 | He et al. | |
| 6,181,287 B1 | 1/2001 | Beigel | |
| 6,330,464 B1 | 12/2001 | Colvin, Jr. et al. | |
| 6,400,974 B1 | 6/2002 | Lesho | |
| 6,440,069 B1 | 8/2002 | Raymond et al. | |
| 6,527,711 B1 | 3/2003 | Stivoric et al. | |
| 6,561,975 B1 * | 5/2003 | Pool et al. | 600/300 |
| 6,561,978 B1 | 5/2003 | Conn et al. | |
| 6,579,498 B1 | 6/2003 | Eglise | |
| 6,646,617 B1 | 11/2003 | Gaukel | |
| 6,694,158 B2 | 2/2004 | Polak | |
| 2002/0026224 A1 * | 2/2002 | Thompson et al. | 607/60 |
| 2003/0119469 A1 | 6/2003 | Karr et al. | |
| 2004/0140939 A1 | 7/2004 | Haller et al. | |

FOREIGN PATENT DOCUMENTS

| | | |
|---|---|---|
| JP | H05-183319 | 7/1993 |
| JP | H07-79467 | 3/1995 |
| JP | H09-36640 | 2/1997 |
| WO | WO 86/03645 A1 | 6/1986 |

* cited by examiner

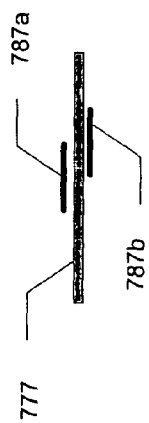
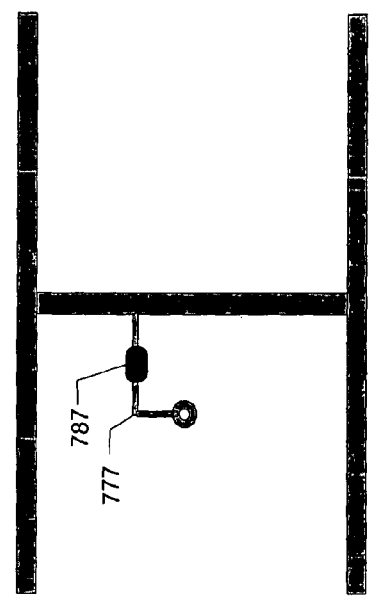
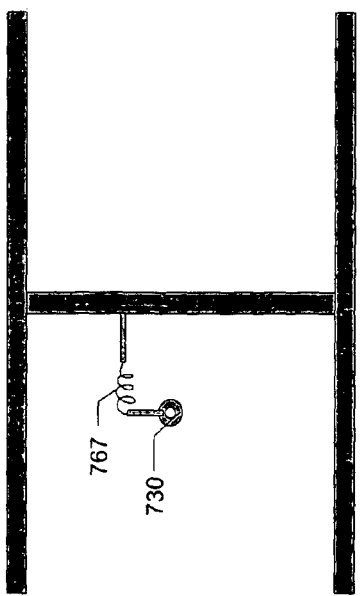

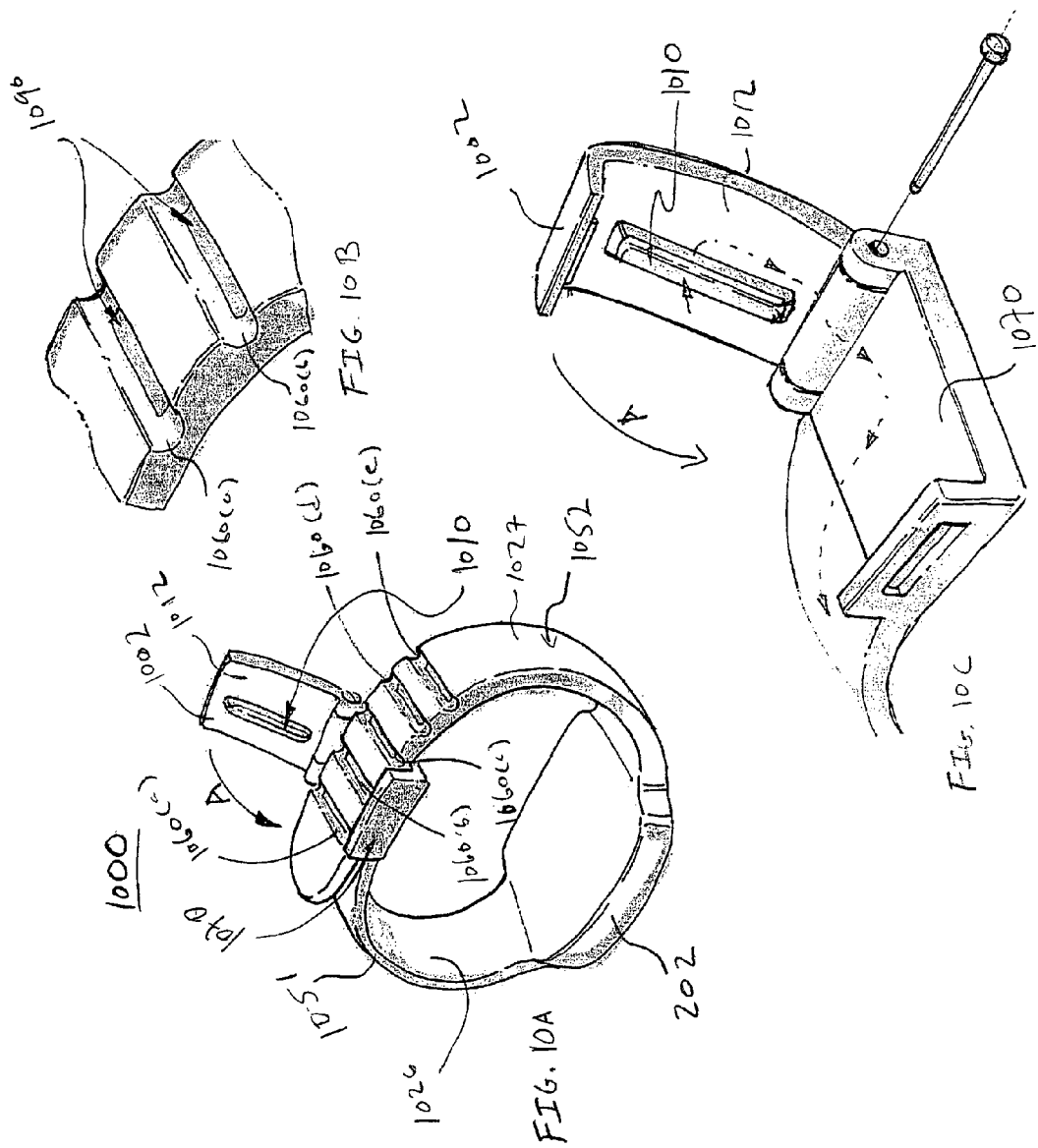

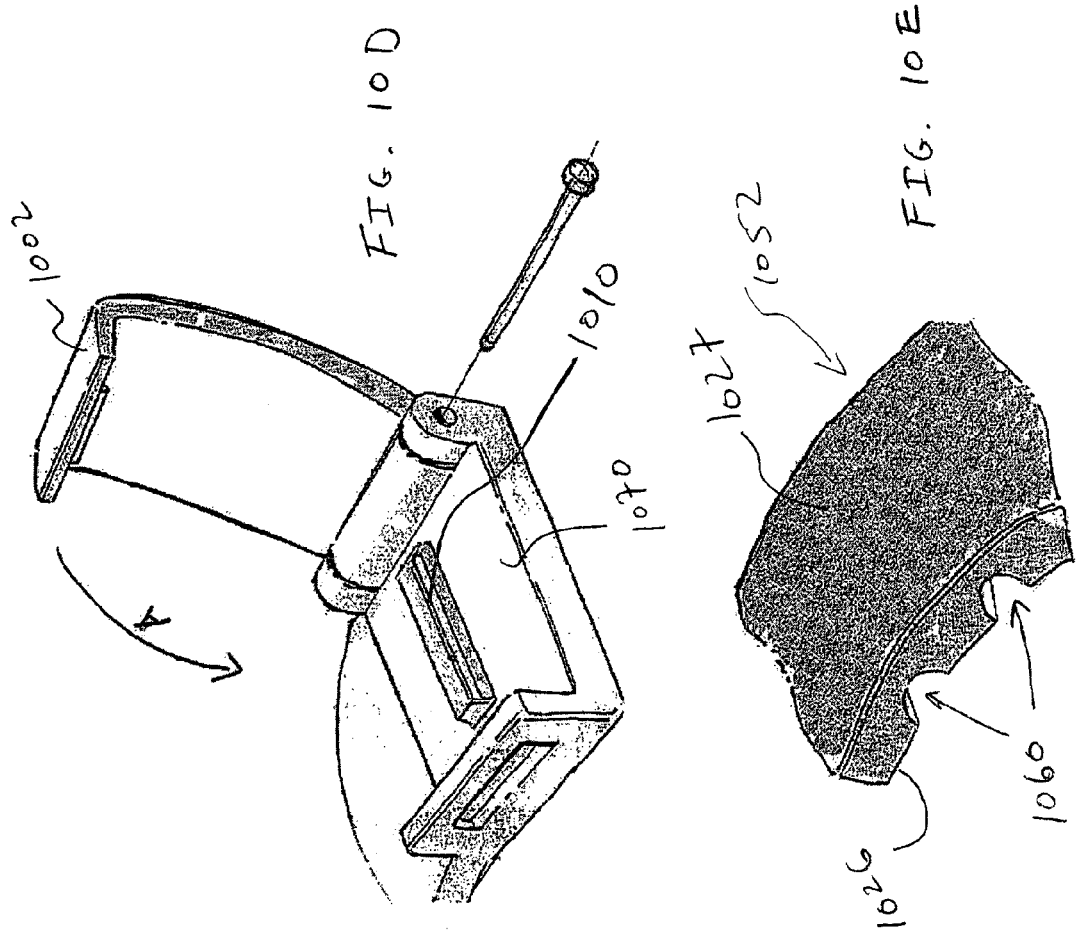

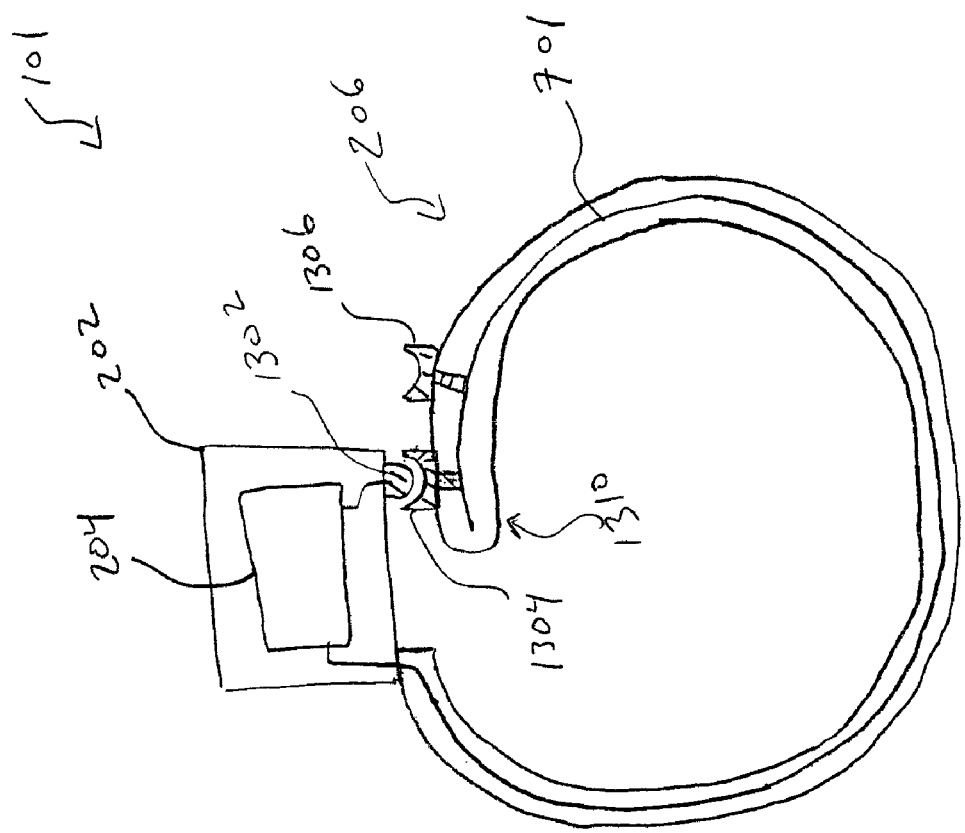

WRISTBAND OR OTHER TYPE OF BAND HAVING AN ADJUSTABLE ANTENNA FOR USE WITH A SENSOR READER

BACKGROUND OF THE INVENTION

1. Field of the Invention

The present invention relates to a wristband or other type of band having an adjustable antenna, and, more specifically, to a wristband or other type of band having an adjustable antenna for use with an external sensor reader that is designed to be worn on a user's wrist or other body part and communicate wirelessly with an implanted sensing device.

2. Discussion of the Background

U.S. Pat. No. 6,400,974 (the "'974 patent"), the disclosure of which is incorporated herein by this reference, discloses an implantable sensor and a sensor reader. The sensor reader is configured to communicate wirelessly with the implanted sensor through a local radio frequency (RF) electromagnetic field. For example, the sensor reader wirelessly supplies power to the sensor, as well as collects data from the sensor. Because the sensor reader communicates wirelessly with the implanted sensor, the sensor reader is typically required to have an antenna.

As used herein, the term "antenna" should be construed broadly to encompass any device that is used in the wireless communication of information and/or the wireless provision of power from one point or device to another point or device. For example, the term antenna is intended to encompass, among other things, one or more components (e.g., one or more pieces of wire and/or other passive or active components) that can be used to generate an electric and/or magnetic field and/or respond to an electric and/or magnetic field.

SUMMARY OF THE INVENTION

In one aspect, the present invention provides a sensor processing system having an implantable sensor and a sensor reader, wherein the sensor reader is designed so that a user of the sensor reader can wear the sensor reader comfortably on the user's wrist or other body part while the sensor reader communicates wirelessly with the sensor. Advantageously, the sensor itself is implanted within the user's wrist or other body part.

In one particular embodiment, the sensor reader includes a housing attached to or integral with a band (e.g., a wristband). The housing contains processing components and the band may have embedded therein an antenna circuit for inductively coupling the sensor reader to one or more elements within the sensor, which antenna circuit may be in the shape of a coil or loop or multiple loops.

In another aspect, the present invention provides a sensor reader having a wristband and a housing connected to the wristband encasing electronic circuitry. The wristband houses an antenna circuit electrically connected to the electronic circuitry. The antenna includes a first electrical circuit disposed in a first half of the wristband and a second electrical circuit disposed in a second half of the wristband. The first electrical circuit is electrically connected to a first contact and the second circuit is electrically connected to a plurality of tuning elements. Each of the tuning elements is electrically connected in series with a second contact configured to receive the first contact. Advantageously, as a result of one of the second contacts receiving the first contact, the first electrical circuit becomes electrically connected to the second electrical circuit through one of the tuning elements.

In another aspect, the present invention provides a sensor reader system that includes a wristband and a housing encasing electronic circuitry. The housing is attached to the wristband. The wristband houses an antenna electrically connected to the electronic circuitry within the housing. The antenna includes a flexible dielectric substrate with a circuit disposed thereon. The circuit includes a first elongate conductor extending from a first region of the substrate to a second region of the substrate along a first side edge of the substrate and a second elongate conductor extending from a third region of the substrate to a fourth region of the substrate along a second side edge of the substrate. The second side edge is opposite the first side edge. The first and second elongate conductors are electrically connected to each other and both the first and third regions are adjacent to a first end of the substrate.

The present invention also provides a sensor reader having a demodulation means for demodulating a signal; a housing for housing the demodulating means; wristband means attached to the housing for enabling a subject to wear the housing on the subject's wrist; and antenna means, integral with the wristband means and coupled to the demodulating means, for communicating with a sensor implanted in the subject's wrist.

The above and other features and advantages of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, help illustrate various embodiments of the present invention and, together with the description, further serve to explain the principles of the invention and to enable a person skilled in the pertinent art to make and use the invention. In the drawings, like reference numbers indicate identical or functionally similar elements. Additionally, the left-most digit(s) of a reference number identifies the drawing in which the reference number first appears.

FIG. 7B illustrates using a discrete inductor as a circuit tuning element.

FIGS. 7C,D illustrate an alternative inductive tuning element.

FIG. 10A illustrates a wristband according to an alternative embodiment of the present invention.

FIGS. 10B and 10C further illustrate portions of the wristband shown in FIG. 10A.

FIGS. 10D and 10E illustrates a variation of the wristband shown in FIG. 10A.

FIG. 13 is a cross-sectional view of a wristband according to an alternative embodiment of the present invention.

DETAILED DESCRIPTION OF PREFERRED EMBODIMENTS

Figure 1:
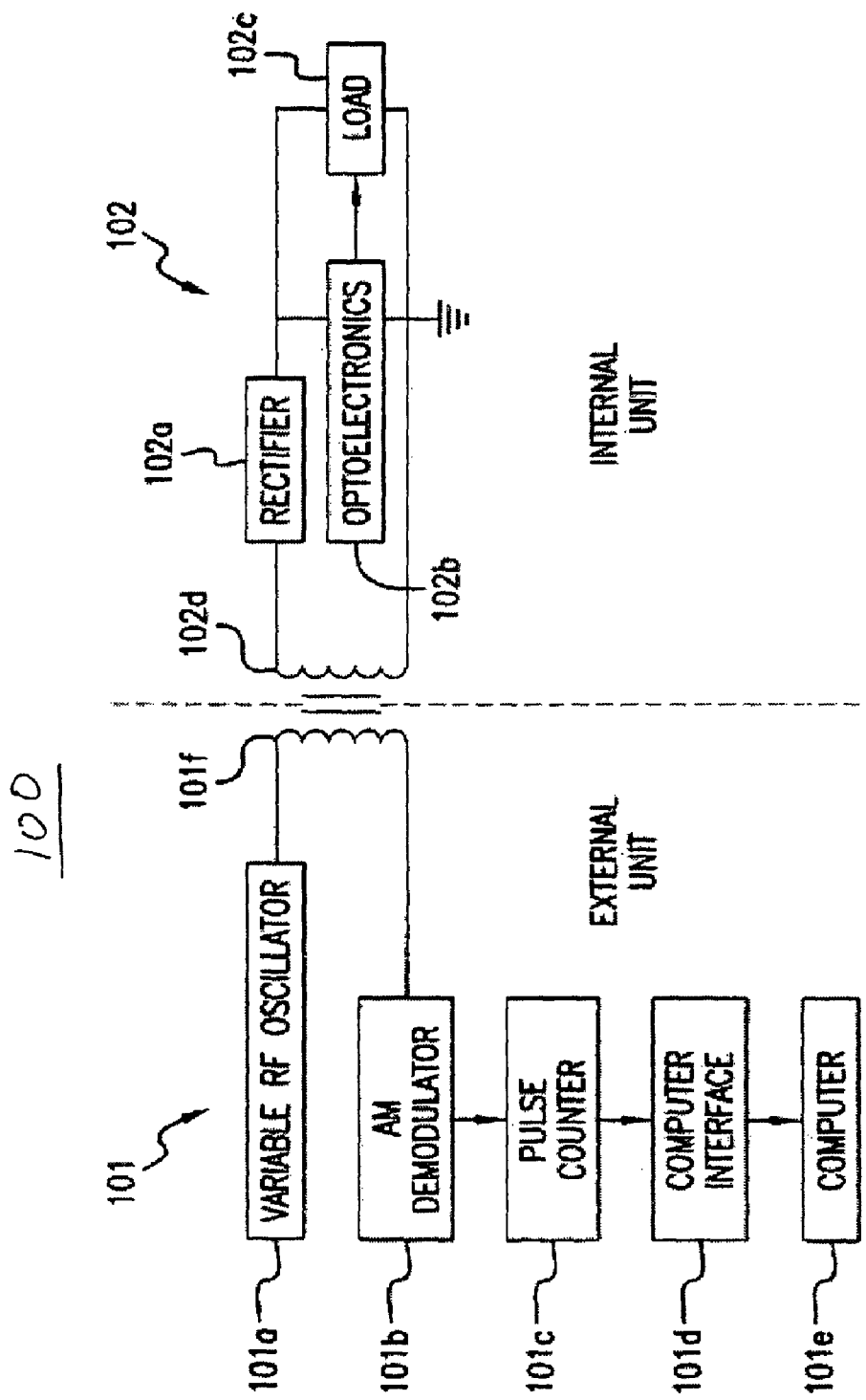
FIG. 1 shows a block diagram of one preferred embodiment of a sensor processing system 100 according to the present invention.

FIG. 1 shows a block diagram of one preferred embodiment of a sensor processing system 100 according to the present invention. System 100 includes a sensor reader 101 (a.k.a., "external unit") and a sensor 102 (a.k.a., "internal unit"). In one example of an application of the system, the internal unit 102 would be implanted either subcutaneously or otherwise within the body of a subject (e.g., in the subject's wrist or other body part). Sensor 102 contains optoelectronics circuitry 102b, a component of which may be comprised of a fluorescence sensing device as described in the '974 patent (discussed above in paragraph [002]).

The optoelectronics circuitry 102b obtains quantitative measurement information and modifies a load 102c as a function of the obtained information. The load 102c in turn varies the amount of current through antenna 102d, which is coupled to an antenna 101f of sensor reader 101. Antennas 102d and 101f are usually in the shape of a coil or loop or multiple loops. A demodulator 101b (for example, an amplitude modulation (AM) demodulator or other demodulator) detects the current variations induced in antenna 101f by antenna 102d coupled thereto, and applies the detected signal to processing circuitry, such as a pulse counter 101c and computer interface 101d, for processing the signal into computer-readable format for inputting to a processor 101e.

An RF oscillator 101a provides an RF signal to antenna 101f, which in turn provides electromagnetic energy to antenna 102d, when the antennas 101f and 102d are within close enough proximity to each other to allow sufficient inductive coupling between the antennas. The energy from the RF signal provides operating power for the sensor 102 to obtain quantitative measurements, which are used to vary the load 102c and in turn provide a load variation to the antenna 101f that is detected by the sensor reader 101 and decoded into information. The load variations are coupled from the sensor 102 to the sensor reader 101 through the mutual coupling between the antennas 101f and 102d.

The loading can be improved by tuning both the internal antenna 102d and the external antenna 101f to approximately the same frequency, and increasing the Q factor of the resonant circuits by appropriate construction techniques. Because of their mutual coupling, a current change in one antenna induces a current change in the other antenna. The induced current is detected and decoded into corresponding information.

Figure 2:
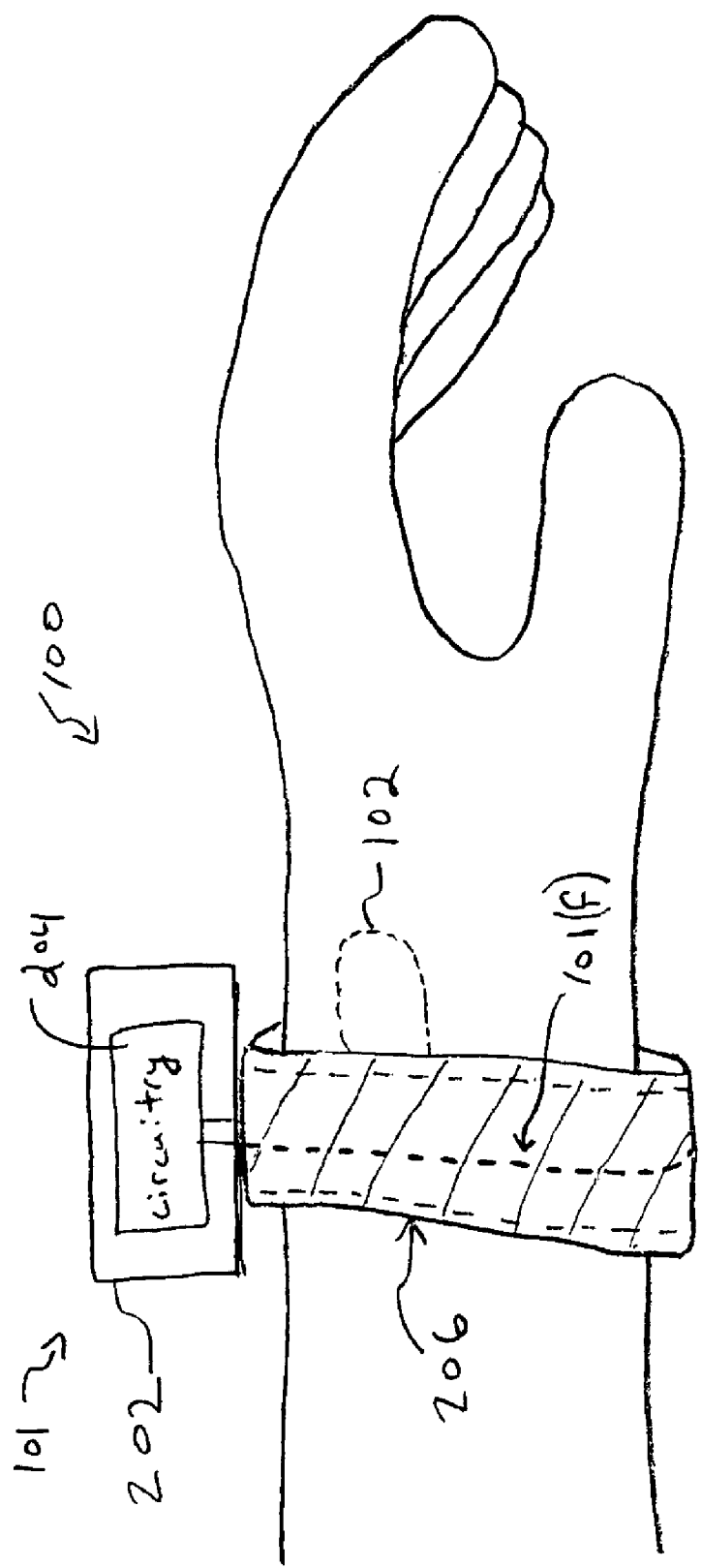
FIG. 2 illustrates an embodiment of sensor processing system 100 according to the present invention.

FIG. 2 illustrates an embodiment of sensor processing system 100. As shown in FIG. 2, the sensor 102 may be implanted within a subject's wrist and the sensor reader 101 may be worn like a watch on the subject's wrist. While the figures described herein illustrate the "wristband" embodiment of the invention, this was only done for the sake of brevity. One of ordinary skill in the art will appreciate that the invention is neither limited to implanting the sensor in the subject's wrist or to a wristband. For example, one of ordinary skill in the art will appreciate that the sensor may be implanted practically anywhere in the users body (e.g., the arm, leg, ankle, neck, etc.). Accordingly, the term "wristband" should be interpreted to cover any type of band, including, for example, armbands, legbands, neckbands, anklebands, etc.

As further shown in FIG. 2, an embodiment of sensor reader 101 includes a reader housing 202, data processing circuitry 204 (for example, AM demodulator 101b, processor 101e, etc.) housed in housing 202, and a wristband 206 to which reader housing 202 is attached. As shown in FIG. 2, antenna 101f of sensor reader 101 is integral with wristband 206 and electrically connected to circuitry 204. The antenna 101f is shown as a dotted line to indicate that the antenna 101f is preferably encased within band 206.

The wristband 206 can be made of any suitable material such as, for example, leather, vinyl, etc. In preferred embodiments, the wristband 206 may provide comfort to the user, an aesthetic appearance, and added strength to the antenna and circuitry.

As discussed above, sensor reader 101 is configured to communicate wirelessly with the implanted sensor 102 through a local radio frequency (RF) electromagnetic field (not shown) to supply power and control to sensor 102, as well as to collect data from sensor 102. It is preferred that the longitudinal axis of antenna 101f be parallel with the axis of antenna 102d of sensor 102. In some embodiments, antenna 101f is a single turn coil. However, antenna 101f may have multiple turns (two or more) or loops or other configurations, as may be required for different power levels and/or operating frequencies.

In preferred embodiments, the wristband 206 is designed so that the user of sensor reader 101 can remove reader 101 from the wrist and put the reader 101 back on the wrist again as with any wristband, such as a conventional wristband for a common watch. For ordinary watches this typically is accomplished by either of two mechanisms. One common design is an elastic band that the user can stretch while removing the watch or putting it on. A second common design is to use a releasable fastening, such as, for example, a clasp or buckle.

In embodiments of the present invention, like a common wristband for a wrist watch, wristband 206 includes a releasable fastening for connecting the ends of the wristband together, thereby securing the wristband on a subject's wrist. However, because electrical continuity must be maintained in antenna 101f, the fastening used in the present invention serves not only to fasten the ends of the band together, but also as an electrical connector to maintain electrical continuity in antenna 101f, as described below.

Figure 3:
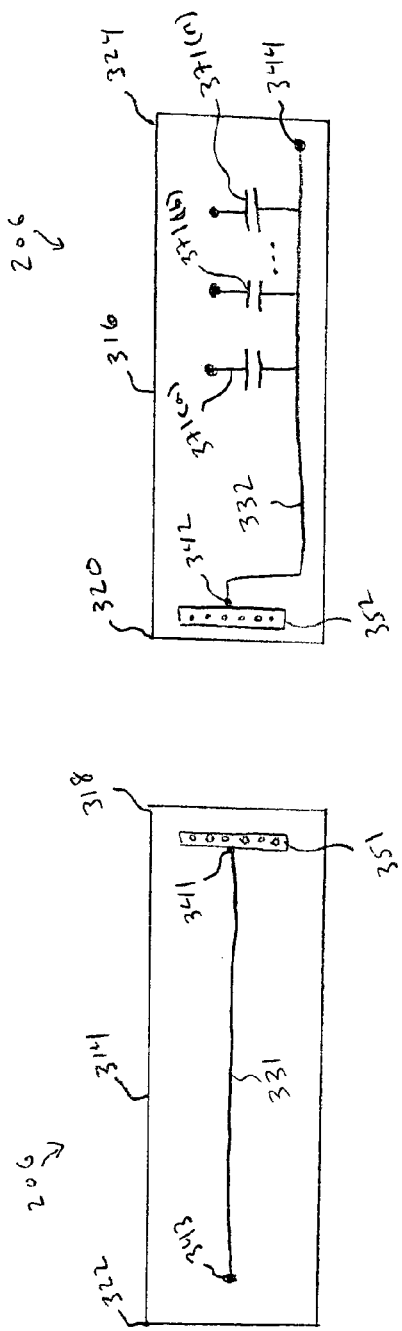
FIG. 3 is a top view of wristband 206 according to some embodiments of the present invention.

FIG. 3 is a top view of wristband 206 according to some embodiments of the invention. The wristband 206 includes elongated first and second wristband portions 314, 316, each adapted to fit part way around a wearer's wrist. The wristband portions have first or proximal ends 318, 320, which are configured to mechanically connect to opposite sides of housing 202. Wristband portions 314, 316 also include second or distal ends 322, 324, which are adapted to be interconnected in overlapping relationship by means of a conductive releasable fastening.

Figure 4:
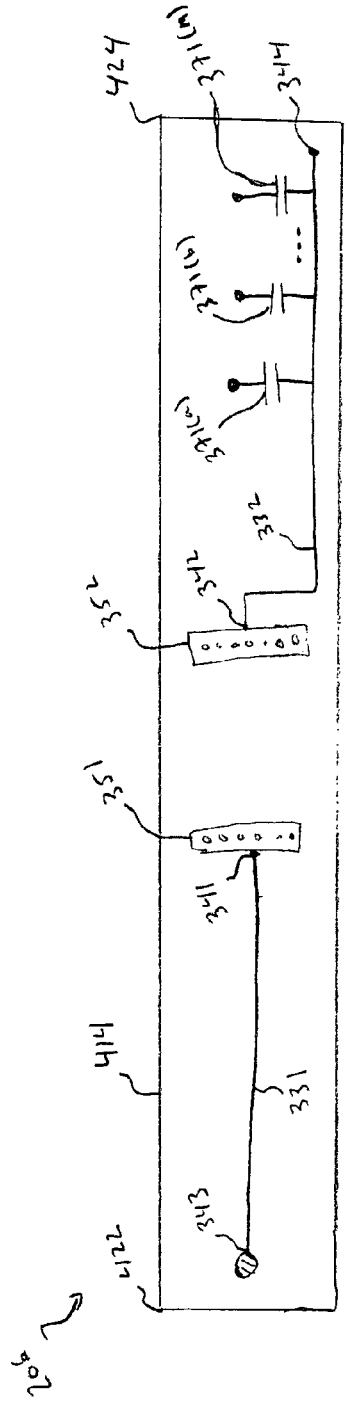
FIG. 4 is a top view of wristband 206 according to some other embodiments of the present invention.

FIG. 4 is a top view of wristband 206 according to some other embodiments of the invention. The wristband 206, in these other embodiments, includes a single elongated wristband portion 414, which is adapted to fit all the way around the wearer's wrist. Preferably, the housing 202, is attached to an outer surface of wristband 206 in a location that places the housing generally in the middle of the wristband portion 414. Wristband portion 414 has a first end 422 and a second end 424, which are adapted to be interconnected in overlapping relationship by means of a conductive releasable fastening (not shown).

As shown in FIGS. 3 and 4, antenna 101f is integrated into wristband 206. In the embodiments shown, antenna 101f is a single turn coil and includes a first elongated electrical conductor 331 and a second elongated electrical conductor 332, both of which are embedded in wristband 206, which is designed to circumscribe a subject's wrist. However, as discussed above, antenna 101f may be a multi-turn coil or other configuration, in which case antenna 101f may include additional electric conductors.

In the embodiment shown in FIG. 3, conductor 331 is embedded in the first wristband portion 314 and conductor 332 is embedded in the second wristband portion 316. Each electrical conductor 331, 332 may include one or more electrical components (e.g., a metallic wire or the like or other circuit component capable of transmitting electricity). The electrical conductors 331, 332 have proximal ends 341, 342 and distal ends 343, 344, respectively. Additionally, electrical conductor 332 is electrically connected to a set of tuning elements 371(a)-(n), which, in a preferred embodiment include capacitors, however, the tuning elements need not be capacitors, but may include inductive elements, a combination of inductors and capacitors or other circuit elements or combination thereof. Although not shown in FIG. 3 or 4, circuitry within housing 202 is electrically connected to proximal ends 341, 342 of conductors 331, 332 through, for example, housing interface attachments 351, 352, respectively.

When wristband 206 is secured around a subject's wrist by a fastening device, conductor 331 will be electrically connected to conductor 332 through one of the capacitors 371(a)-(n), thereby completing the antenna 101f, which now circumscribes the subject's wrist. This is illustrated in FIG. 5.

Figure 5:
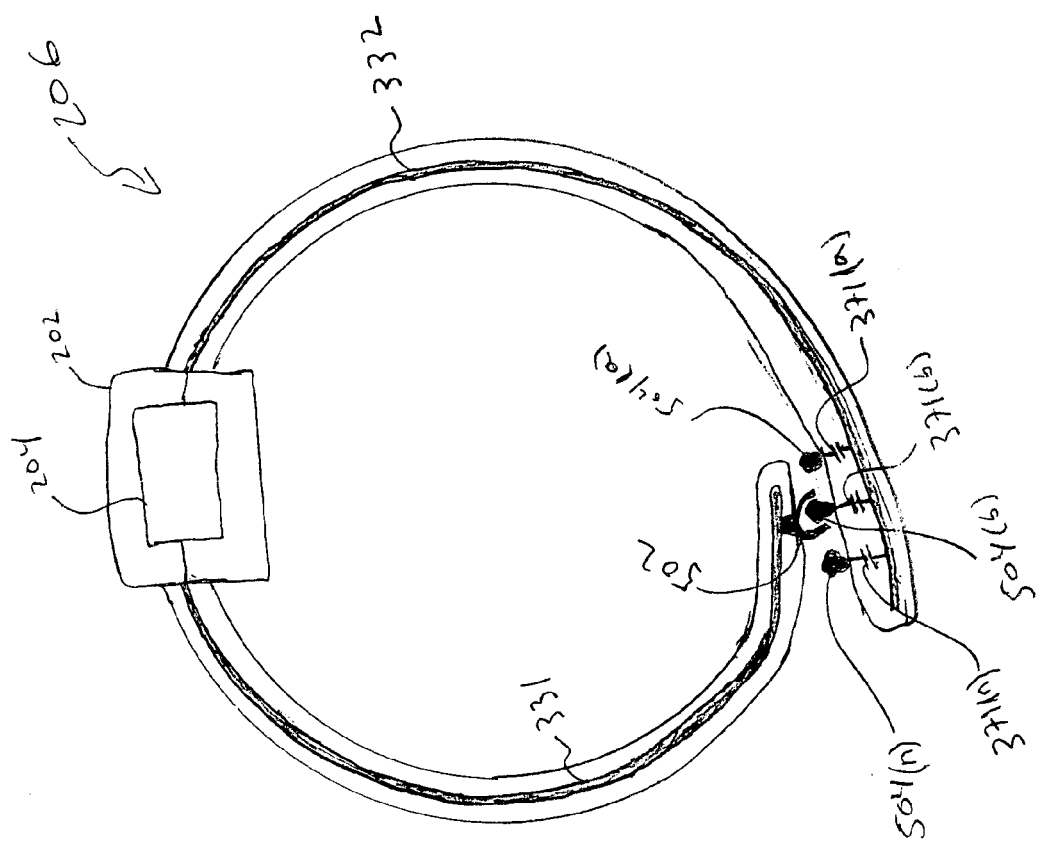
FIG. 5 is a cross-sectional view of wristband 206 when the wristband is worn on a subject's wrist.

FIG. 5 is a cross-sectional view of wristband 206, according to some embodiments of the invention, when the wristband is worn on a subject's wrist. As shown in FIG. 5, electrical conductor 331 is in electrical contact with a first electrical contact 502. In the embodiment shown, electrical contact 502 is the female half of a snap. However, electrical contact 502 may be any male or female contact element or even a simple conductive pad.

Similarly, electrical conductor 332 is in electrical contact with a set of electrical contacts 504(a)-(n) through capacitors 371(a)-(n), respectively. That is, capacitor 371(a) is connected between contact 504(a) and conductor 332, capacitor 371(b) is connected between contact 504(b) and conductor 332, and capacitor 371(n) is connected between contact 504(n) and conductor 332. In the embodiment shown in FIG. 5, each contact 504 is the male half of a snap. However, as with contact 502, each contact 504 may be any male or female contact element or even a simple conductive pad. Contact 502 is configured to mate with any one of contacts 504(a)-(n), and thereby electrically connect conductor 331 with conductor 332, as shown in FIG. 5.

Preferably, each capacitor 371 has a different capacitance. And preferably, the capacitances of capacitors 371 are selected such that antenna 101f will have the same electrical properties regardless of which contact 504(a)-(n) contact 502 mates with. That is, the capacitors 371 are preferably chosen so that the electrical properties of antenna 101f are same whether contact 502 mates with contact 504(a), 504(b) or 504(n). For example it is preferred that the resonant frequency of the antenna circuit remain substantially unchanged regardless of the corresponding contact with which contact 502 mates.

Figure 6:
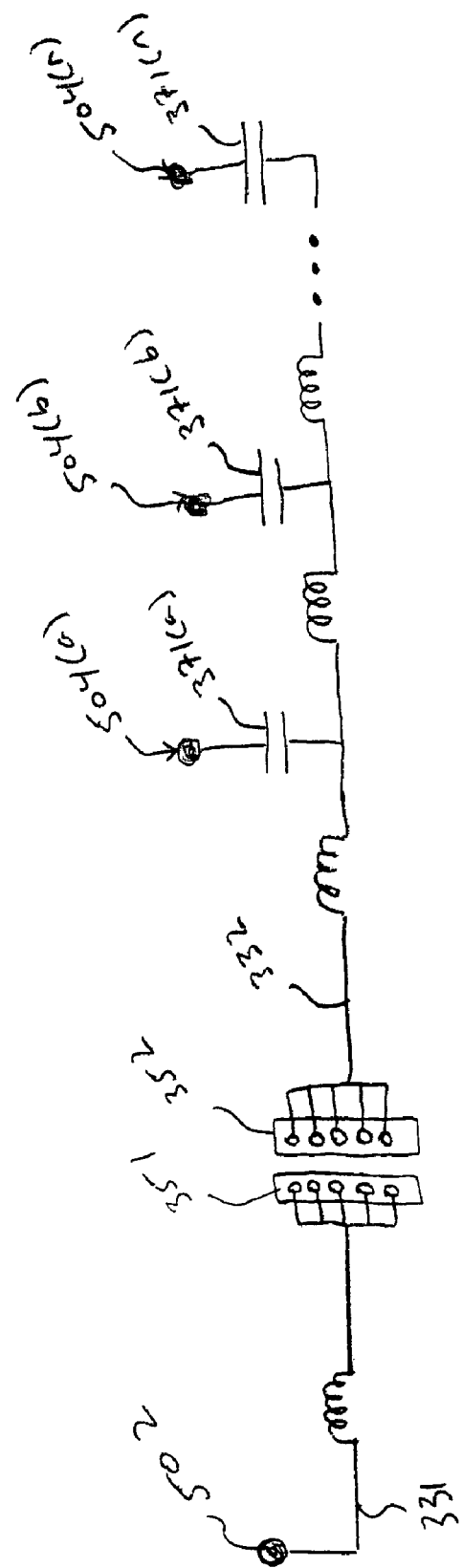
FIG. 6 illustrates a circuit schematic of the wristband shown in FIG. 5.

FIG. 6 illustrates a circuit schematic of the wristband shown in FIG. 5. The circuit schematic illustrates how each capacitor 371 is connected in series between a contact 504, and conductor 332. The schematic also illustrates that when contact 502 is connected to a contact 504, the contacts 502 and 504 provide an electrical path between conductors 331, 332. The inductors shown in FIG. 6 are not discrete components like capacitors 371 and connectors 502, 504. The inductors shown in FIG. 6 represent the inductance of the conductors 331, 332.

Figure 7A:
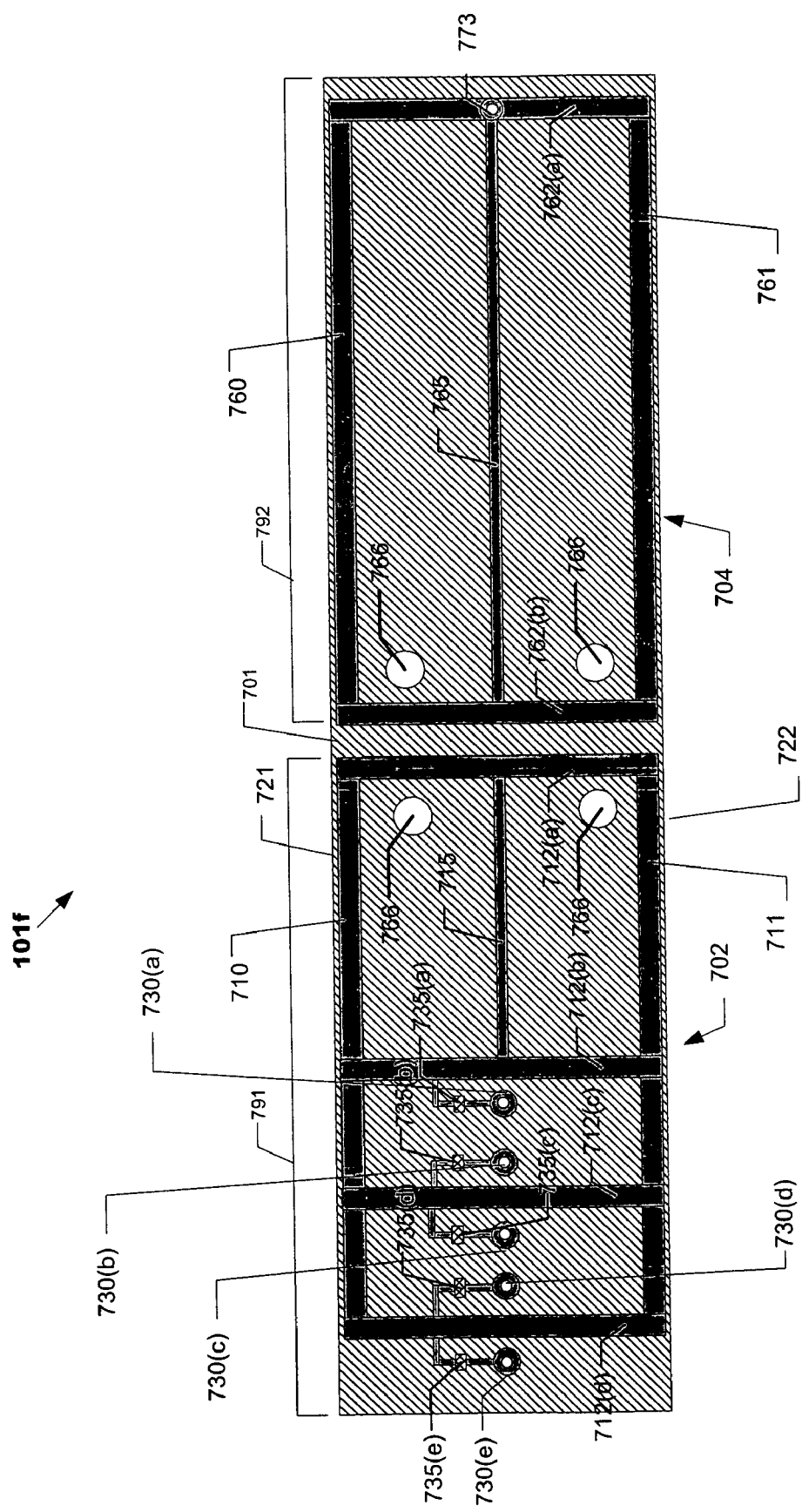
FIG. 7A illustrates an antenna according to one embodiment of the present invention.

FIG. 7A illustrates another design for antenna 101f. In the embodiment shown in FIG. 7A, antenna 101f may be implemented using a flexible dielectric substrate 701 (a.k.a., "circuit board" 701) having elongate electrical conductors, conductive pads and other electrical components disposed thereon. Preferably, the circuit board 701 is encased within a conventional wristband material (e.g., leather, vinyl, etc) (not shown) to produce wristband 206. Preferably, the width of the resulting wristband 206 is equal to or just slightly greater than the width of circuit board 701, which width is preferably about ¾ of an inch. In alternative embodiments, the width of wristband 206 may be larger or smaller.

In the embodiment shown in FIG. 7A, antenna 101f includes a first circuit 702 located on a first portion 791 of circuit board 701 and a second circuit 704 located on a second portion 792 of board 701. In the embodiment shown, first portion 791 includes substantially the entire right/left half of board 701 and second portion 792 includes substantially the entire left/right half of board 701. As also shown in FIG. 7A, first portion 791 is directly connected to or integral with second portion 792. However, other embodiments wherein first and second portions 791, 792 are not directly connected or integral are contemplated. In some embodiments, board 701 and the conductors and components disposed thereon are covered or coated with a flexible dielectric lamina.

Referring now to first circuit 702, first circuit 702 includes: (1) a first longitudinal, elongate conductor 710 that extends lengthwise from generally one end of the first portion 791 of board 701 to the other end of the first portion 791, as shown in FIG. 7A; (2) a second longitudinal, elongate conductor 711 that is spaced apart from the first conductor 710 and that also extends lengthwise from generally one end of the first portion 791 to the other end of the first portion 791; and (3) one or more transverse conductors 712 that electrically connect first conductor 710 with second conductor 711. For example, transverse conductor 712(c) has a first end connected to conductor 710 and a second end connected to conductor 711, thereby electrically connecting conductor 710 with conductor 711.

Preferably, conductor 710 and 711 extend adjacent to a first side edge 721 and a second side edge 722 of board 701, respectively, as shown in FIG. 7A. More specifically, conductor 710 extends along side edge 721 and conductor 711 extends along side edge 722. Each conductor 710, 711 may include one or more electrical components (e.g., a metallic wire or the like or other circuit components capable of transmitting electricity).

Circuit 702 may further include one or more conductive pads 730. Each conductive pad 730 is electrically connected to conductors 710 and 711 through one or more circuit tuning elements 735. For instance, in some embodiments, each pad 730 is electrically connected to conductors 710 and 711 through a circuit tuning element 735 that is electrically connected between the pad 730 and a transverse conductor 712.

For example, pad 730(c) is electrically connected to conductors 710 and 711 via tuning element 735(c) and transverse conductor 712(c).

In one embodiment, each tuning element 735 is a single discrete capacitor having a predetermined capacitance, however, as described above, each tuning element 735 may include multiple capacitors, inductors and/or other circuit elements. For example, in some alternative embodiments, the tuning elements 735 are discrete inductive tuning elements that are chosen such that the total inductance remains constant regardless of the size at which the wristband is set. This feature is illustrated in FIG. 7B, which shows using a discrete inductor 767 as a tuning element In some other embodiments, for example, as shown in FIG. 7C, tuning element 735 may include a trace stub 777 and one or more pieces of ferrite 787 disposed on or around the trace stub 777. FIG. 7D is a cross sectional view that further illustrates this feature.

As shown in FIG. 7D, one or more pieces of ferrite or other like inductance tuning parts are disposed above and/or below trace stub 777. In this example embodiment, the inductance of the stub 777 depends on the amount of ferrite and the location of the ferrite relative to the stub. The location may be adjusted during the manufacturing process to provide a desired inductance in the stub. For at least some stubs 777, a single piece of ferrite on one side thereof may be sufficient, while two pieces as shown in FIG. 7D will provide greater inductance when needed. It should be noted that ferrite pieces 787 could be disposed above and/or below a transverse conductor 712 instead of above and/or below the trace stub 777 that connects a pad 730 to the transverse conductor 712.

The ferrite operates the same as a discrete inductor, adjusting the total inductance through each path so that the antenna inductance and tuned resonance remain constant regardless of the selected wrist band size. The choice of a tuning element (e.g., discrete inductors, discrete capacitors, ferrite pieces, etc.) depends mostly on which is easiest and least expensive to manufacture, since they are all functionally similar.

In embodiments where tuning elements 735 are inductive tuning elements, reader 101 may include a capacitive tuning element that is tuned permanently to match the inductance of the largest adjustment size, with the antenna inductance (including series inductive devices) remaining constant regardless what wristband size adjustment is selected.

When using inductive tuning elements, as opposed to capacitive tuning elements, the current through the wristband, and presumably the magnetic field near the wristband, remains the same regardless of the size selected for the wristband. The variable capacitive tuning method tends to draw as much current as possible for each size of the wristband. Whether it is more advantageous to use inductive or capacitive tuning elements depends on how much magnetic field is needed for maximum range without overloading the sensor at maximum coupling.

Conductive pads 730 function to electrically connect a conductive fastening element to circuit 702. For example, in one embodiment, attached to each pad 730 is a male or female half of a snap.

As further shown in FIG. 7A, circuit 702 may further include one or more auxiliary conductors. The auxiliary conductors are disposed between conductors 710, 711 and generally parallel thereto. In the embodiment shown in FIG. 7A, one auxiliary conductor 715 is shown. Conductor 715 is positioned between transverse conductors 712(a) and 712(b), with one end of conductor 715 being connected to transverse conductor 712(a) and the other end being connected to transverse conductor 712(b). Preferably, the width (w1) of the auxiliary conductors is less than the width (w2, w3) of the edge conductors 710, 711, respectively. For example, in some embodiments, the width of conductors 710, 711 is generally twice the width of the auxiliary conductors. More formally, in some embodiments $w2=w3=>2w1$. Additionally, in some embodiments, the length of conductor 715 is less than the length of conductors 710, 711, which may be equal in length. As illustrated in FIG. 7A, the length of one embodiment of conductor 715 is between ¼ and ¾ of the length of conductors 710 and 711, which are equal in length and which are typically between 4 and 6 inches.

Referring now to second circuit 704, circuit 704 includes: (1) a first longitudinal, elongate conductor 760 that extends lengthwise from generally one end of the second portion 792 of board 701 to the other end of the second portion 792, as shown in FIG. 7A; (2) a second longitudinal, elongate conductor 761 that is spaced apart from the first conductor 760 and that also extends lengthwise from generally one end of the second half of board 701 to the other end of the second half of board 701; and (3) one or more transverse conductors 762 that electrically connect first conductor 760 with second conductor 761. For example, transverse conductor 762(a) has a first end connected to conductor 760 and a second end connected to conductor 761, thereby electrically connecting conductor 760 with conductor 761. Preferably, conductors 760 and 761 extend adjacent to the first side edge 721 and the second side edge 722 of board 701, respectively, as shown in FIG. 7A.

Circuit 704 may further include one or more conductive pads. In the embodiment shown, circuit 704 includes one conductive pad 773. Conductive Pad 773 is disposed on top of and is electrically connected to transverse conductor 762(a). Pad 773 functions to electrically connect a conductive fastening element to circuit 704. For example, in one embodiment, attached to pad 773 is a male or female half of a snap, depending on what type of snap is attached to pads 730. For example, if male snaps are attached to pads 730, then a female snap would be attached to pad 773.

As further shown in FIG. 7A, circuit 704 may further include one or more auxiliary conductors. The auxiliary conductors are spaced between conductors 760, 761 and are generally parallel thereto. In the embodiment shown in FIG. 7A, one auxiliary conductor 765 is shown. Conductor 765 is positioned between transverse conductors 762(a) and 762(b), with one end of conductor 765 being connected to conductor 762(a) and the other end being connected to conductor 762(b). Preferably, the width of the auxiliary conductors is less than the width of the edge conductors 760, 761. For example, in some embodiments, the width of conductors 760, 761 is generally twice the width of the auxiliary conductors. However, the length of conductor 765 may be equal to the length of conductors 760, 761 as illustrated in FIG. 7A.

Figure 8:
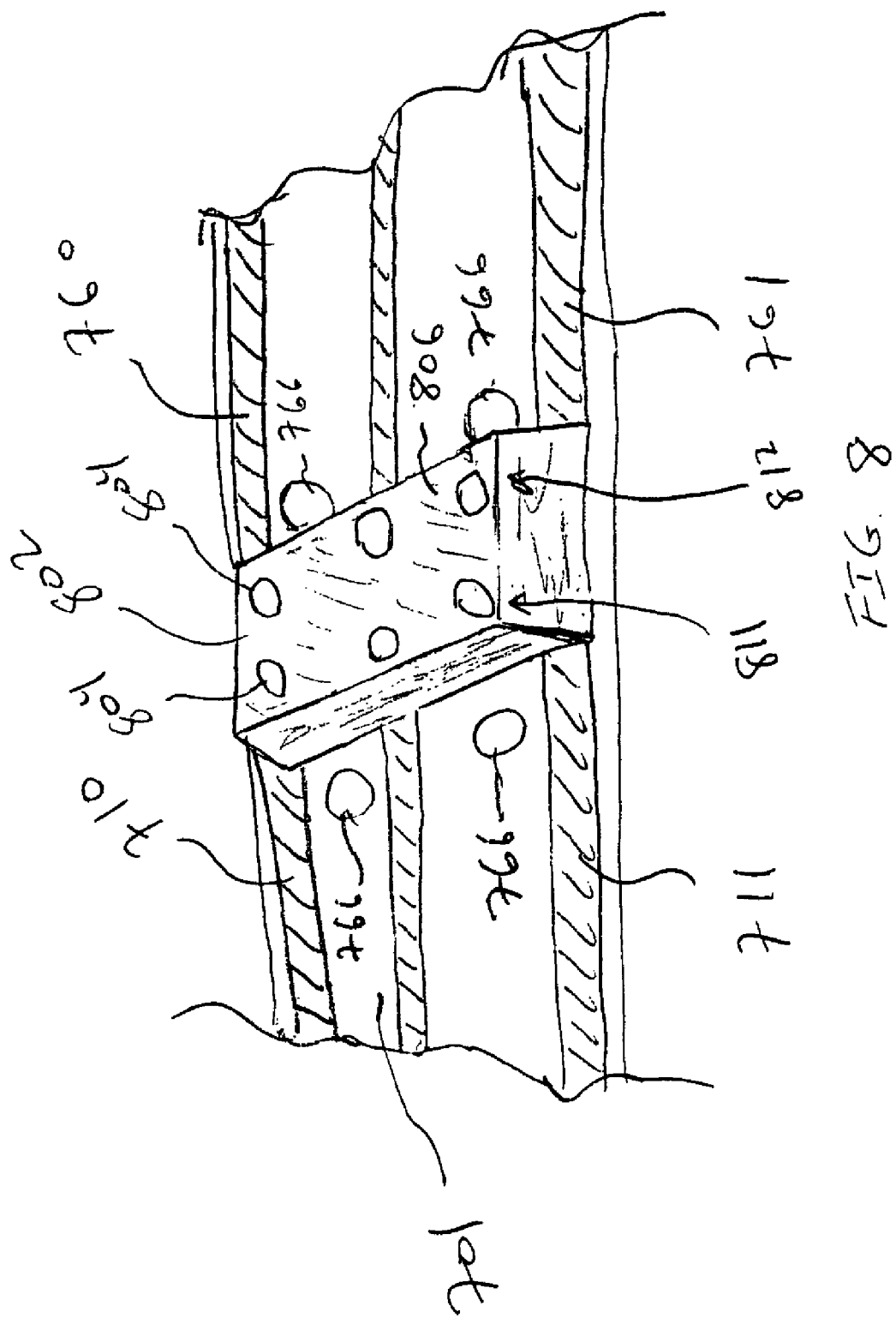
FIG. 8 illustrates a connector according to one embodiment for connecting a sensor reader to the antenna shown in FIG. 7A.

Referring now to FIG. 8, FIG. 8 illustrates one possible way to electrically connect electronic circuitry within reader 101 to the antenna circuitry on board 701. In the example embodiment shown, connected to board 701 is a connector housing 802 for connecting electronic circuitry within reader 101 to the antenna circuitry on board 701. In some embodiments, as shown in FIG. 8, housing 802 sits on transverse conductors 712(a) and 762(b), which are adjacent to each other. Connector housing 802 is designed to provide a means for easily connecting electronic circuitry within reader 101 to antenna circuits 702 and 704. Connector housing 802 is preferably made of a dielectric material.

It should be noted that in some embodiments the connector housing 802 or the like is not used at all. That is, the reader 101 may be directly soldered to one or more of the conductors on board 701, thereby making the connector 802 unnecessary. In other alternative embodiments, a reader circuit board on which the reader circuitry is disposed could include the antenna. For example, the reader circuit board could have one or two flexible portions for the antenna; the reader circuit board could have an area overlapping the antenna for mounting the reader parts; and the reader circuit board could have a parts mounting area that could be made substantially thicker than an antenna portion (i.e., the parts mounting area of the circuit board can be rigid instead of flexible, while the antenna portion of the circuit board is flexible instead of rigid).

The embodiment of housing 802 shown in FIG. 8 has a number of apertures 804 preferably arranged in two columns 811 and 812. Each aperture extends from a top surface 806 of housing 802 to the bottom surface of the housing. Disposed partially in each aperture is an electrically conducting contact element (not shown). That is, one end of the contact element is within the aperture and the other end extends beyond the bottom surface of the housing. The end that extends beyond the bottom surface of the housing is electrically connected to either circuit 702 or 704. For example, an electrical contact located within an aperture that is part of the first column of apertures 811 is physically and electrically connected to transverse conductor 712(a), and an electrical contact located within an aperture that is part of the second column of apertures 812 is connected to transverse conductor 762(a).

Referring back to FIG. 7A, an advantage of having conductors 710, 711, 760 and 761 be located adjacent the respective side edges of board 701 is that such a configuration produces an electromagnetic field that is wider than the width of the wristband. A wider electromagnetic field is advantageous because it allows for lateral movement of the wristband on the user's wrist with respect to the implanted sensor while maintaining communication with the implanted sensor. If there was not such a wide field, then movement of the wristband would be more likely to result in a loss of communication because the sensor may no longer be within the field generated by the antenna. This feature is illustrated in FIG. 9.

Figure 9:
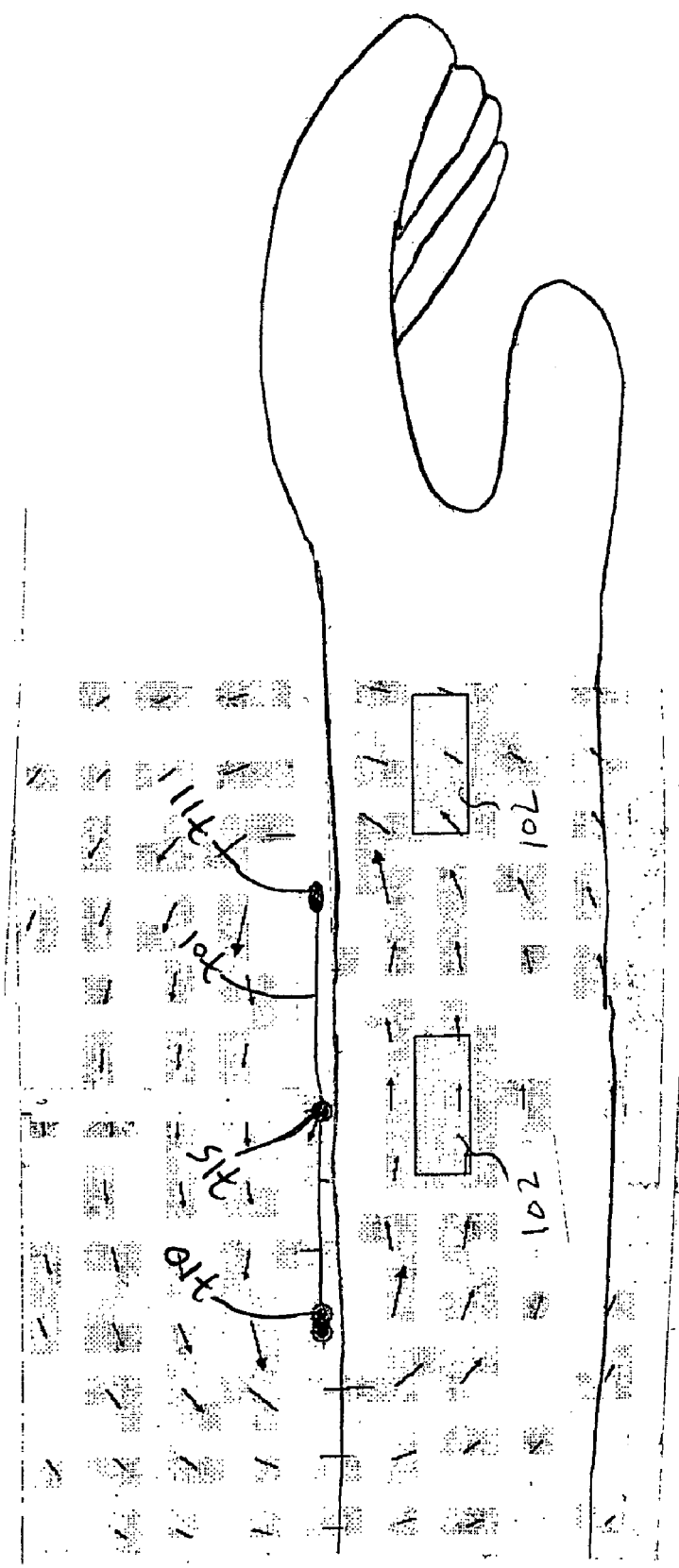
FIG. 9 illustrates an exemplary electromagnetic field generated by an antenna according to an embodiment of the present invention.

FIG. 9 is a cross sectional view of antenna 101f according to the embodiment shown in FIG. 7A. FIG. 9 shows the electromagnetic field generated by the antenna 101f. As shown in FIG. 9, the width of the field is greater than the width of the wristband, which is generally the distance between conductors 710 and 711 (or conductors 760, 761), which width is generally about ¾ of an inch. When the width between conductors 710 and 711 is about ¾ of an inch the width of the resulting electromagnetic field may be up to two (2) inches.

The rectangular box shown in FIG. 9 represents the implanted sensor. Accordingly, FIG. 9 illustrates that antenna 101f can move laterally with respect to the sensor a short distance and the sensor will still be within the field generated by the antenna. Thus, even if the antenna 101f were to move laterally a short distance on the user's wrist because the wristband housing the antenna is worn loose on the user's wrist, the sensor reader will not lose communication with the sensor. The wider electromagnetic field is advantageous for an additional reason that the width of wristband may be made smaller, and thus more aesthetically pleasing to some users, without jeopardizing functionality.

Figure 12:
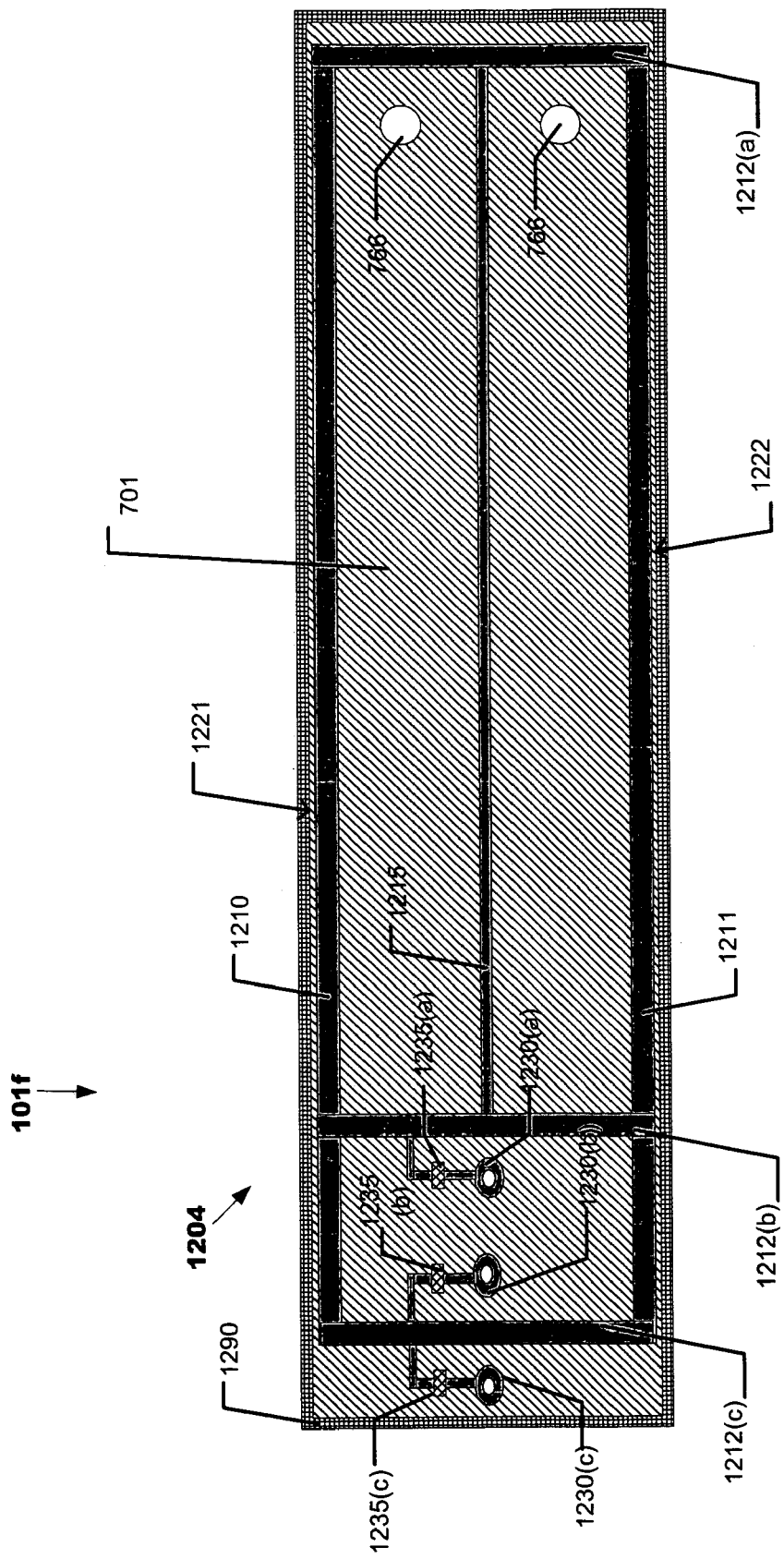
FIG. 12 illustrates an antenna according to another embodiment of the present invention.

FIG. 12 illustrates another design for antenna 101f. In the embodiment shown in FIG. 12, antenna 101f may be implemented using the dielectric substrate 701 with elongate electrical conductors, conductive pads and other electrical components disposed thereon. Preferably, the circuit board 701 is encased within a conventional wristband material 1290 (e.g., leather, vinyl, etc) to produce wristband 206. Preferably, the width of the resulting wristband 206 is equal to or just slightly greater than the width of circuit board 701, which width is preferably about ¾ of an inch. The antenna according to the embodiment shown in FIG. 12, is similar to the antenna shown in FIG. 7A. A difference between the two embodiments is that in the first embodiment (FIG. 7A) the reader housing 202 is attached generally in the middle of circuit board 701, whereas in the second embodiment (FIG. 12), the reader is attached to the ends of circuit board 701 as illustrated in FIG. 13.

Referring back to FIG. 12, the antenna 101f according to the embodiment shown includes a circuit 1204. Circuit 1204 includes: (1) a first longitudinal, elongate conductor 1210 that extends lengthwise from generally one end of board 701 to the other end of board, as shown in FIG. 12; (2) a second longitudinal, elongate conductor 1211 that is spaced apart from the first conductor 1210 and that also extends lengthwise from generally one end of board 701 to the other; and (3) one or more transverse conductors 1212. Like transverse conductors 712 and 762, each transverse conductor 1212 has one end in contact with the first elongate conductor 1210 and the other end in contact with the second elongate conductor 1211. For example, transverse conductor 1212(a) has a first end connected to conductor 1210 and a second end connected to conductor 1211, thereby electrically connecting conductor 1210 with conductor 1211. Preferably, conductors 1210 and 1211 extend adjacent to the first side edge 1221 and the second side edge 1222 of board 701, respectively, as shown in FIG. 12.

Circuit 1204 may further include one or more conductive pads 1230. Each conductive pad 1230 is electrically connected to conductors 1210 and 1211 through one or more circuit elements 1235. For instance, in some embodiments, each pad 1230 is electrically connected to conductors 1210 and 1211 through a circuit element 1235 that is electrically connected between the pad 1230 and a transverse conductor 1212. For example, pad 1230(c) is electrically connected to conductors 1210 and 1211 via capacitor 1235(c) and transverse conductor 1212(c). In the embodiment shown, element 1235 is a capacitor having a predetermined capacitance. Conductive pads 1230 function to electrically connect a conductive fastening element to circuit 1204. For example, in one embodiment, attached to each pad 1230 is a male or female half of a snap.

As further shown in FIG. 12, circuit 1204 may further include one or more auxiliary conductors. The auxiliary conductors are disposed on board 701 and between conductors 1210, 1211 and generally parallel thereto. In the embodiment shown in FIG. 12, one auxiliary conductor 1215 is shown. Conductor 1215 is positioned between transverse conductors 1212(a) and 1212(b), with one end of conductor 1215 being connected to conductor 1212(a) and the other end being connected to conductor 1212(b). As discussed above, preferably, the width of the auxiliary conductors is less than the width of the edge conductors 1210, 1211. However, the length of conductor 1215 may be equal to the length of conductors 1210, 1211, although in the embodiment shown the length of conductor 1215 is less than the length of the primary conductors 1210, 1211.

Referring now to FIG. 13, FIG. 13 is a cross-sectional view of wristband 206, according to alternative embodiments of the invention, when the wristband is worn on a subject's wrist. As shown in FIG. 13, contact elements 1304, 1306 are attached to the wristband. Contact elements 1304, 1306 are female contact elements, however male or other contact elements could be used. Contact elements 1304, 1306 are electrically connected to the circuit on circuit board 701. More specifically, they may be electrically connected in series with a pad 1230 (not shown). As further shown in FIG. 13, a corresponding contact element 1302 may be attached to housing 202. Contact element 1302 is electrically connected to circuitry 204. Contact elements 1304, 1306 are designed to mate with contact element 1302, thereby completing a circuit and releasably attaching end 1310 of band 206 to housing 202. The opposite end of band 206 may be fixedly attached to housing 202. Hence, screw holes 766 are provided in board 701 so that housing 202 may be screwed to board 701 (see FIGS. 7, 8 and 12).

Figure 11:
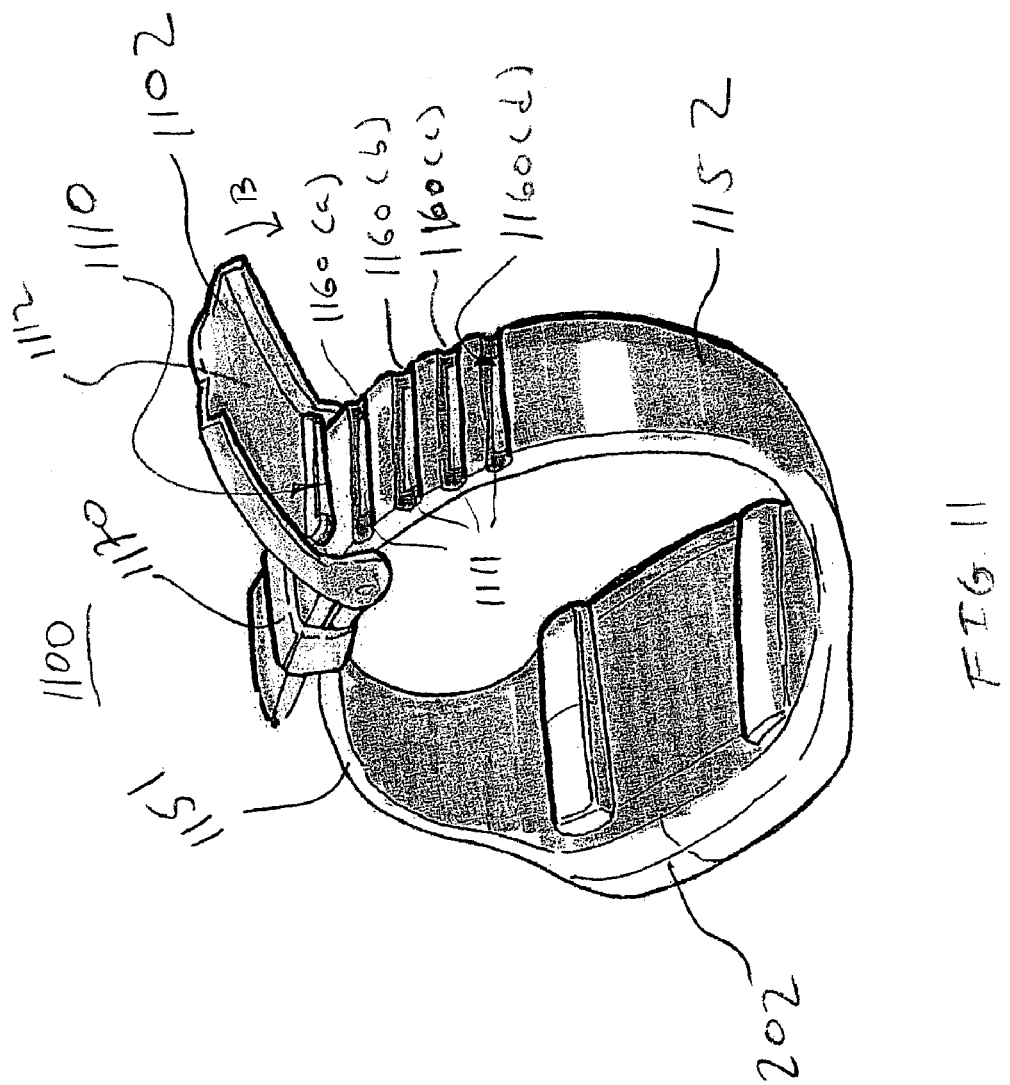
FIG. 11 illustrates a wristband according to an alternative embodiment of the present invention.

FIGS. 10 and 11 illustrate wristbands according to alternative embodiments of the present invention. The wristbands shown in FIGS. 10 and 11 are similar to the others shown herein, the differences primarily being in the clasping mechanism for securing the wristband on a subject's wrist.

Referring now to FIG. 10A, FIG. 10A shows a wristband 1000 having a first wristband portion 1051 and a second wristband portion 1052. A lock tab 1002 is attached to a distal end of the first wristband portion 1051. Lock tab 1002 is rotatably attached to one edge of wristband portion 1051 and is free to rotate around an axis that is substantially parallel with a longitudinal axis of wristband portion 1051.

A male electrical contact 1010 projects outwardly from the bottom face 1012 of lock tab 1002. Preferably, contact 1010 is elongate and is oriented on lock tab 1002 such that the longitudinal axis of contact 1010 is substantially parallel with a longitudinal axis of lock tab 1002.

Although not shown in FIG. 10A, a first portion of antenna 101f (e.g., circuit 704 or conductor 331) is embedded within first wristband portion 1051 and is electrically connected to the male electrical contact 1010. Additionally, a second portion of antenna 101f (e.g., circuit 702 or conductor 332) is embedded within second wristband portion 1052. Second wristband portion 1052 has a set of transverse grooves 1060 (a)-(e) on an outer surface 1027 thereof (i.e., the surface that faces away from the subjects wrist when the watch is worn as intended). As shown in FIG. 10B, each groove 1060 includes an exposed electrical contact 1090. Like electrical contacts 504 and pad 730, each exposed electrical contact 1090 is connected in series with a capacitive structure which itself is connected in series with the antenna portion. Hence, the antenna portion is electrically connected to each electrical contact 1090 through a capacitive structure.

Wristband 1000 is secured to a subject's wrist by inserting the distal end of wristband portion 1052 into a catch 1070 (see also FIG. 10C) and rotating lock tab 1002 in the direction of arrow A so that male electrical contact 1010 is disposed in one of the grooves 1060. When wristband 1000 is secured in this manner, the exposed contact 1090 in the groove 1060 receives the male contact 1010, thereby, electronically connecting the first portion of the antenna to the second portion of the antenna.

FIG. 10D illustrates a variation of the design. As shown in FIG. 10D, contact 1010 may be disposed on the outer surface of catch 1070 and project outwardly therefrom. In this embodiment, transverse grooves 1060 are on the inner surface 1026 of second wristband portion 1052, as opposed to the outer surface, as shown in FIG. 10E.

Referring now to FIG. 11, FIG. 11 shows a wristband 1100 having a first wristband portion 1151 and a second wristband portion 1152. A lock tab 1102 is attached to a distal end of the first wristband portion 1151. Lock tab 1102 is rotatably attached to both edges of wristband portion 1151 and is free to rotate around an axis that is substantially perpendicular with respect to a longitudinal axis of wristband portion 1151.

A male electrical contact 1110 projects outwardly from the bottom face 1112 of lock tab 1102. Preferably, contact 1110 is elongate and is oriented on lock tab 1102 such that the longitudinal axis of contact 1110 is substantially parallel with a transverse axis of lock tab 1102.

Although not shown in FIG. 11, a first portion of antenna 101f is embedded within first wristband portion 1151 and is electrically connected to the male electrical contact 1110. Additionally, a second portion of antenna 101f is embedded within second wristband portion 1152. Second wristband portion 1152 has a set of transverse grooves 1160(a)-(d) on an outer surface thereof. Each groove 1160 includes an exposed electrical contact 1111. Like electrical contacts 1090, each exposed electrical contact 1111 is connected in series with a capacitive structure which itself is connected in series with the antenna portion. Hence, the antenna portion is electrically connected to each electrical contact 1111 through a capacitive structure.

Wristband 1100 is secured to a subject's wrist by inserting the distal end of wristband portion 1152 into a catch 1170 and rotating lock tab 1102 in the direction of arrow B so that male electrical contact 1110 is disposed in one of the grooves 1160. When wristband 1100 is secured in this manner, the exposed contact 1111 in the groove in which male contact 1110 is disposed receives the male contact 1110, thereby, electrically connecting the first and second portions of antenna 101f.

While various embodiments/variations of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A sensor system, comprising:
   a sensor, adapted to be implanted in a subject, wherein the sensor is configured to measure one or more aspects of the subject and wherein the sensor comprises a sensor antenna;
   a sensor reader configured to provide power to the sensor, wherein the sensor reader is adapted to be worn by the subject and comprises:
   (i) a reader housing containing an electronic circuit;
   (ii) a reader antenna for coupling with the sensor antenna, wherein the reader antenna is electrically coupled to the electronic circuit, forms a coil having at least one turn when wound completely around a body part of the subject, is adjustable in size to any of a plurality of adjustment sizes, and is used by the sensor reader while the at least one turn of the coil is wound completely around the body part of the subject to provide power to the sensor; and
   (iii) a plurality of tuning elements each associated with a different size of the plurality of adjustment sizes;
   wherein the reader antenna has a resonant frequency and the plurality of tuning elements keep the resonant frequency of the reader antenna substantially unchanged regardless of the adjustment size to which the reader antenna is adjusted.

2. The sensor system of claim 1, wherein each tuning element of the plurality of tuning elements is a capacitive element or an inductive element.

3. The sensor system of claim 2, wherein the capacitive element comprises at least one capacitor and the inductive element comprises at least one inductor.

4. The sensor system of claim 2, wherein the inductive element comprises ferrite that is adjacent to and/or surrounding a conductor electrically connected to the reader antenna.

5. The sensor system of claim 2, wherein the plurality of tuning elements have different capacitive values and/or different inductive values.

6. A sensor reader, comprising:
   (i) a reader housing containing an electronic circuit;
   (ii) a reader antenna for coupling with an antenna of a sensor, wherein the reader antenna:
      (a) is electrically coupled to the electronic circuit,
      (b) comprises a first end and a second end that are releasably and adjustably attachable to each other and attach to form a closed-loop coil having one of a plurality of adjustment sizes and at least one turn,
      (c) has a resonant frequency, and
      (d) is used by the sensor reader while the first and second ends are attached and the at least one turn of the closed-loop coil formed thereby is wound completely around a body part of a subject to provide power to the sensor; and
   (iii) a plurality of tuning elements each associated with a different size of the plurality of adjustment sizes;
   wherein the plurality of tuning elements keep the resonant frequency of the reader antenna substantially unchanged regardless of the adjustment size to which the reader antenna is adjusted, and
   wherein said sensor reader is adapted to be worn by the subject.

7. The sensor system of claim 6, wherein each tuning element of the plurality of tuning elements is a capacitive element or an inductive element.

8. The sensor system of claim 7, wherein the capacitive element comprises at least one capacitor and the inductive element comprises at least one inductor.

9. The sensor system of claim 7, wherein the inductive element comprises ferrite that is adjacent to and/or surrounding a conductor electrically connected to the reader antenna.

10. The sensor system of claim 7, wherein the plurality of tuning elements have different capacitive values and/or different inductive values.

* * * * *